(12) United States Patent
Bi et al.

(10) Patent No.: US 12,364,780 B2
(45) Date of Patent: Jul. 22, 2025

(54) NAVIGATION METHOD FOR DISINFECTION ROBOT, ROBOT AND COMPUTER-READABLE STORAGE MEDIUM

(71) Applicant: UBTECH ROBOTICS CORP LTD, Shenzhen (CN)

(72) Inventors: Zhanjia Bi, Shenzhen (CN); Youjun Xiong, Shenzhen (CN); Huan Tan, Shenzhen (CN)

(73) Assignee: UBTECH ROBOTICS CORP LTD, Shenzhen (CN)

( * ) Notice: Subject to any disclaimer, the term of this patent is extended or adjusted under 35 U.S.C. 154(b) by 288 days.

(21) Appl. No.: 18/120,990

(22) Filed: Mar. 13, 2023

(65) Prior Publication Data

US 2023/0285619 A1    Sep. 14, 2023

(30) Foreign Application Priority Data

Mar. 14, 2022  (CN) .......................... 202210250018.1

(51) Int. Cl.
*A61L 2/24*     (2006.01)
*G01C 21/00*    (2006.01)

(52) U.S. Cl.
CPC ............ *A61L 2/24* (2013.01); *G01C 21/3807* (2020.08); *G01C 21/3881* (2020.08); *A61L 2202/14* (2013.01); *A61L 2202/16* (2013.01)

(58) Field of Classification Search
None
See application file for complete search history.

(56) References Cited

U.S. PATENT DOCUMENTS 11,352,071 B1 * 6/2022 Ebrahimi Afrouzi .................
                                                         G05D 1/0217
2018/0373242 A1  12/2018 Han
                         (Continued)

FOREIGN PATENT DOCUMENTS

| CN | 109984689 A | 7/2019 |
| CN | 111813111 A | 10/2020 |
| CN | 113359743 A | 9/2021 |

(Continued)

*Primary Examiner* — Vivek D Koppikar
*Assistant Examiner* — David Ruben Pedersen

(57) ABSTRACT

A navigation method for a disinfection robot includes: obtaining an initial map within a field of view of the robot; generating a disinfection grid having multiple disinfection squares on the initial map, and determining multiple disinfecting consideration points in the disinfection squares; determining a disinfection order of disinfecting targets corresponding to the disinfection squares according to distances between the robot after the robot completes disinfection of one of the targets corresponding to one of the disinfection squares and to-be-disinfected ones of the disinfection squares; according to distances between the position and the disinfecting consideration points in to-be-disinfected ones of the disinfection squares, combined with priority levels of the disinfecting consideration points in to-be-disinfected ones of the disinfection squares, determining disinfecting planning points in the disinfection squares; and performing disinfection to the targets corresponding to the disinfection squares according to the disinfection order and the disinfecting planning points.

20 Claims, 5 Drawing Sheets

(56) References Cited

U.S. PATENT DOCUMENTS

2021/0286368 A1* 9/2021 Jung .................... A01D 34/008
2022/0088237 A1* 3/2022 Hauser ................. G06T 15/506

FOREIGN PATENT DOCUMENTS

CN        113566800 A    10/2021
WO    WO-2021139165 A1 *  7/2021  ........... G01C 21/005

* cited by examiner

NAVIGATION METHOD FOR DISINFECTION ROBOT, ROBOT AND COMPUTER-READABLE STORAGE MEDIUM

CROSS REFERENCE TO RELATED APPLICATIONS

This application claims priority to Chinese Patent Application No. CN 202210250018.1, filed Mar. 14, 2022, which is hereby incorporated by reference herein as if set forth in its entirety.

TECHNICAL FIELD

The present disclosure generally relates to robots, and particularly to a navigation method for a disinfection robot and a disinfection robot.

BACKGROUND

A disinfection robot is an indoor intelligent and autonomous robot designed for indoor virus prevention. One type of disinfection robot includes a disinfection system installed inside the robot that can generate disinfection gas, and the spraying system of the robot can quickly spray the disinfection gas in an indoor space. Another type of robot performs disinfection using ultraviolet light, which can effectively increase the coverage, uniformity and effectiveness of disinfection.

Some conventional disinfection robots need to build a map of the disinfecting scene before disinfecting. For example, the SLAM technology can be used to build the map in advance. Alternatively, for efficiency reasons, the map construction process can be completed by a remote-controlled robot moving in the disinfecting scene. However, this approach of separating the mapping from the disinfecting process is not conducive to improving the disinfection efficiency, and it is relatively troublesome to manually control the robot to move in the disinfecting scene in order to build a map.

Therefore, there is a need to provide a navigation method for a disinfection robot to overcome the above-mentioned problem.

BRIEF DESCRIPTION OF DRAWINGS

Many aspects of the present embodiments can be better understood with reference to the following drawings. The components in the drawings are not necessarily drawn to scale, the emphasis instead being placed upon clearly illustrating the principles of the present embodiments. Moreover, in the drawings, all the views are schematic, and like reference numerals designate corresponding parts throughout the several views.

DETAILED DESCRIPTION

Figure 1:
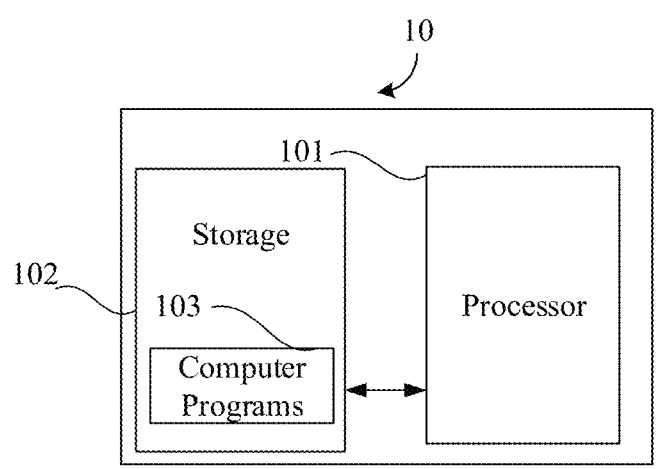
FIG. 1 is a schematic block diagram of a disinfection robot according to one embodiment.

The disclosure is illustrated by way of example and not by way of limitation in the figures of the accompanying drawings, in which like reference numerals indicate similar elements. It should be noted that references to "an" or "one" embodiment in this disclosure are not necessarily to the same embodiment, and such references can mean "at least one" embodiment.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

When a conventional robot performs disinfection in a completely unknown closed environment, it usually needs to first build a scene map of the environment. Then, based on the built scene map, path planning can be performed, and the scene disinfection can then be performed according to the planned path. This approach separates the map building from the disinfecting process, which makes the disinfecting process more troublesome and is not conducive to improving the disinfecting efficiency.

Figure 2:
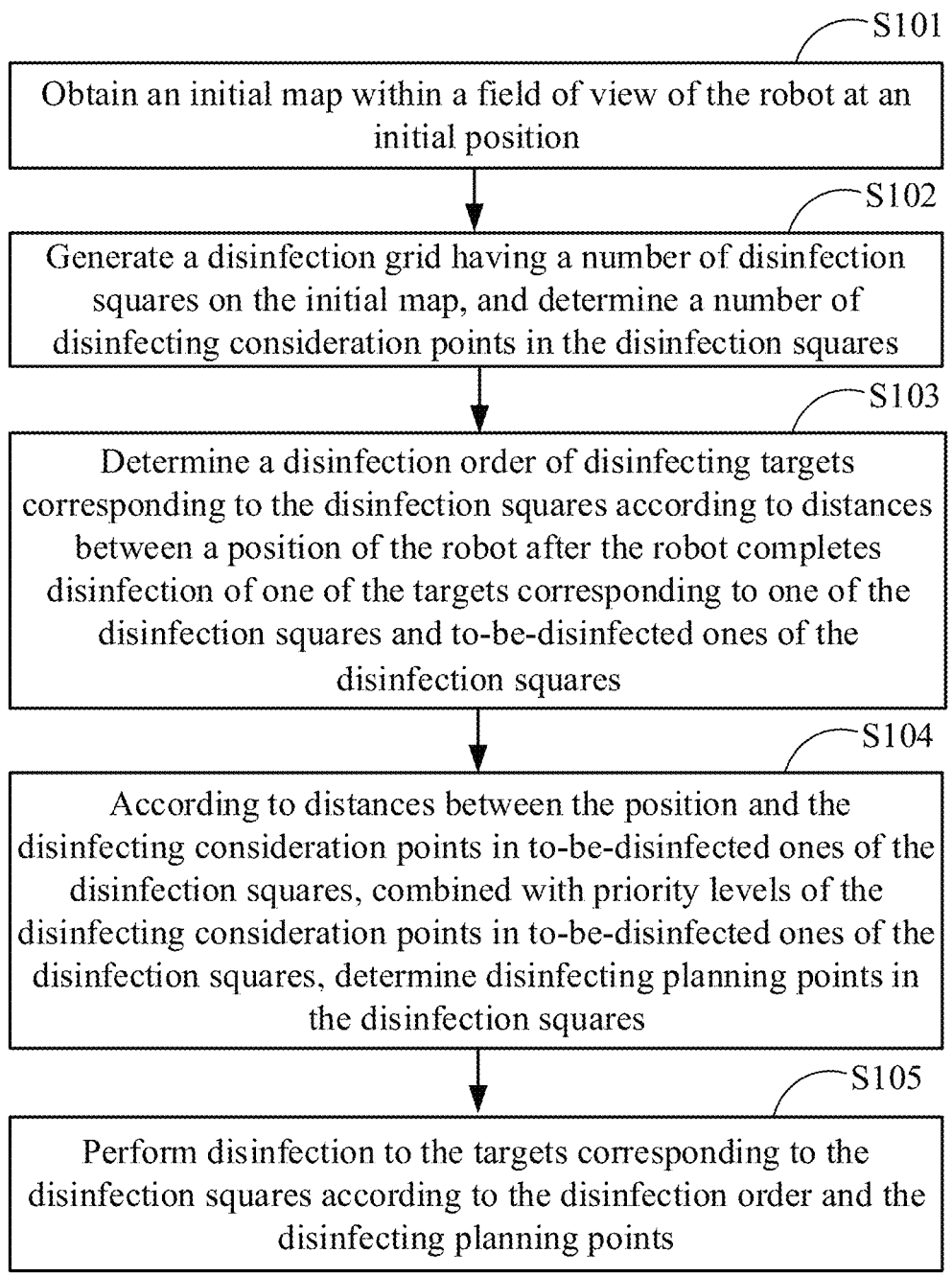
FIG. 2 is an exemplary flowchart of a navigation method for a disinfection robot according to one embodiment.

FIG. 1 shows a schematic block diagram of a disinfection robot 10 according to one embodiment. The robot may include a processor 101, a storage 102, and one or more executable computer programs 103 that are stored in the storage 102. The storage 102 and the processor 101 are directly or indirectly electrically connected to each other to realize data transmission or interaction. For example, they can be electrically connected to each other through one or more communication buses or signal lines. The processor 101 performs corresponding operations by executing the executable computer programs 103 stored in the storage 102. When the processor 101 executes the computer programs 103, the steps in the embodiments of the method for controlling the robot, such as steps S101 to S105 in FIG. 2, are implemented.

The processor 101 may be an integrated circuit chip with signal processing capability. The processor 101 may be a central processing unit (CPU), a general-purpose processor, a digital signal processor (DSP), an application specific integrated circuit (ASIC), a field-programmable gate array (FPGA), a programmable logic device, a discrete gate, a transistor logic device, or a discrete hardware component. The general-purpose processor may be a microprocessor or any conventional processor or the like. The processor 101 can implement or execute the methods, steps, and logical blocks disclosed in the embodiments of the present disclosure.

The storage 102 may be, but not limited to, a random-access memory (RAM), a read only memory (ROM), a programmable read only memory (PROM), an erasable programmable read-only memory (EPROM), and an electrical erasable programmable read-only memory (EEPROM). The storage 102 may be an internal storage unit of the robot, such as a hard disk or a memory. The storage 102 may also be an external storage device of the robot, such as a plug-in hard disk, a smart memory card (SMC), and a secure digital (SD) card, or any suitable flash cards. Furthermore, the storage 102 may also include both an internal storage unit and an external storage device. The storage 102 is used to store computer programs, other programs, and data required by the robot. The storage 102 can also be used to temporarily store data that have been output or is about to be output.

Figure 5:
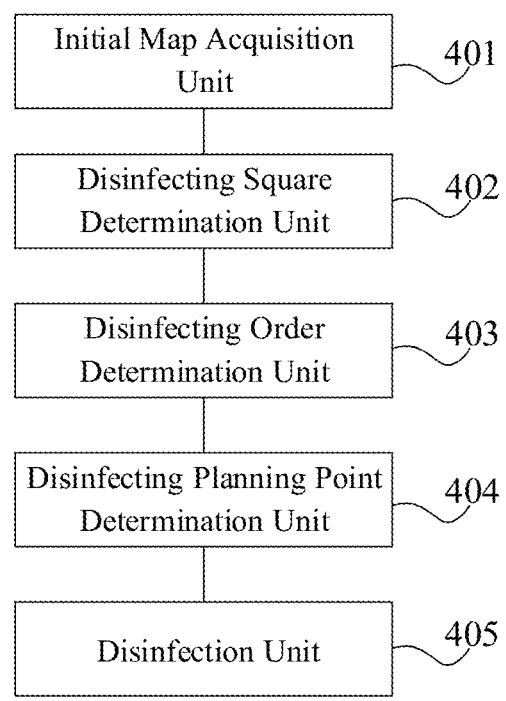
FIG. 5 is schematic block diagram of a disinfection robot according to one embodiment.

Exemplarily, the one or more computer programs 103 may be divided into one or more modules/units, and the one or more modules/units are stored in the storage 102 and executable by the processor 101. The one or more modules/ units may be a series of computer program instruction segments capable of performing specific functions, and the instruction segments are used to describe the execution process of the one or more computer programs 103 in the robot. For example, the one or more computer programs 103 may be divided into an initial map acquisition unit 401, a disinfecting square determination unit 402, a disinfecting order determination unit 403, a disinfecting planning point determination unit 404, and a disinfection unit 405 as shown in FIG. 5.

It should be noted that the block diagram shown in FIG. 1 is only an example of the robot. The robot may include more or fewer components than what is shown in FIG. 1, or have a different configuration than what is shown in FIG. 1. Each component shown in FIG. 1 may be implemented in hardware, software, or a combination thereof.

FIG. 2 is a schematic flowchart of a navigation method for the disinfection robot according to one embodiment. The method may include the following steps.

Step S101: Obtain an initial map within a field of view of the robot at an initial position.

Specifically, the initial position in the embodiment of the present disclosure may be any position in a scene that needs to be disinfected by the robot. The scene may be a scene that needs to be disinfected or sterilized. In one embodiment, the initial position may be the center position in the scene to be disinfected.

When the robot obtains the initial map, it can use a sensing device (e.g., a lidar) arranged in the robot to capture images, and build the initial map in the scene based on the captured images and obstacle information in the scene.

In one embodiment, a lidar may be arranged on the top of the robot, so that the robot can effectively collect map information in the scene. When constructing the initial map, the robot can be controlled to rotate in situ for one revolution to collect complete scene map information.

When the scene map information is collected, the main direction in which the robot travels can also be determined according to the collected scene map information. The main direction may be a direction perpendicular to a wall in the scene. The main direction can be used as the initial movement direction of the robot when starting the disinfection of the scene, and when the subsequent disinfection grid generated, it can be generated according to this direction. For example, the horizontal or vertical sides of the squares of the disinfection grid (see FIG. 3) can be perpendicular to the main direction. As a result, the squares of the disinfecting grid can better match the scene, making the path of the robot more reasonable and complete during the disinfecting process.

The obtained initial map includes obstacle areas and free-moving areas in the scene.

It should be noted that during the process of the robot performing the disinfecting task, the sensing device can continuously collect the map information in the scene, and improve the initial map according to the collected map information.

Step S102: Generate a disinfection grid having a number of disinfection squares on the initial map, and determine a number of disinfecting consideration points in the disinfection squares.

Figure 3:
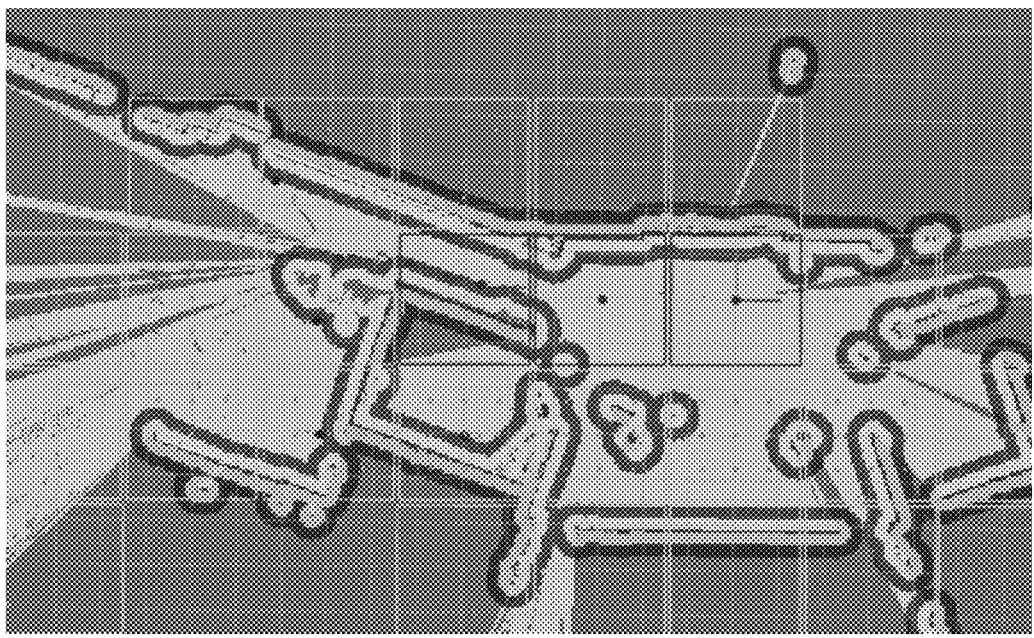
FIG. 3 is a schematic diagram of disinfection squares generated on an initial map.

Referring to FIG. 3, in one embodiment, the disinfection grid can be generated based on the main direction. For example, the horizontal or vertical sides of the squares of the disinfection grid can be perpendicular to the main direction. At least a portion of the disinfection squares are in the known areas of the scene. For example, the center portion of the disinfection grid and at least one vertex of the disinfection grid can be made in the known areas. The known areas may include obstacle areas and/or free-moving areas of the initial map.

The size of the disinfection squares can be determined according to the coverage density of disinfection planning point. The higher the density of the disinfection planning points, the shorter the sides of each disinfection square, and the lower the density of the planning point, the longer the sides of each disinfection square.

The disinfecting consideration points refer to the positions where the robot can perform disinfection to the target corresponding to each disinfection square when planning a path for the robot. Generally, multiple disinfecting consideration points are included in each disinfection square, and different priorities can be set for them. One of the disinfecting consideration points in each disinfection square can be selected as a disinfecting planning point according to the position of the robot.

Figure 4:
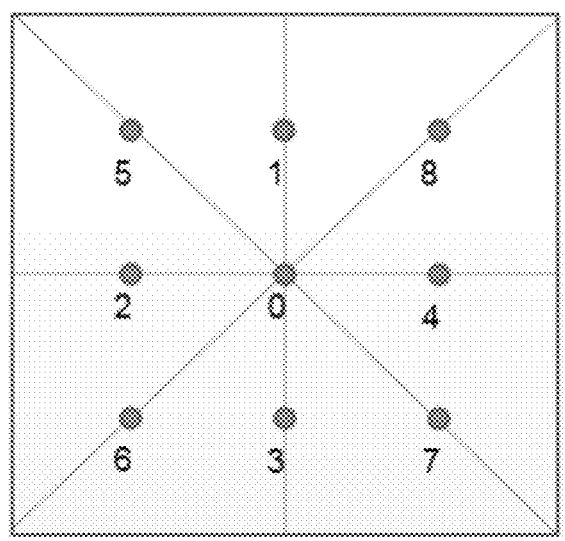
FIG. 4 is a schematic diagram of a disinfection square with its disinfecting consideration points.

In one embodiment, three priority levels can be set for the disinfecting consideration points in each disinfection square. That is, the disinfecting consideration points in each disinfection square may include first-priority disinfecting consideration points, second-priority disinfecting consideration points, and third-priority disinfecting consideration points. For example, as shown in FIG. 4, a total of 9 disinfecting consideration points numbered 0-8 can be set in each disinfection square. Specifically, the center point of each disinfection square (i.e., the disinfecting consideration point numbered 0) can be the first-priority disinfecting consideration point. The disinfecting consideration points at the midpoints of the line segments from the center point to the midpoints of the four sides of the disinfection square (i.e., the disinfecting consideration points numbered 1-4) can be the second-priority disinfecting consideration points. The disinfecting consideration points numbered 5-8 on the midpoints of the line segments between the center point and the vertices can be the third-priority disinfecting consideration points.

The disinfecting consideration points may be the positions where disinfection can be performed to the target corresponding to each disinfection square when the robot performs the disinfection. The disinfecting planning point may be a position that is calculated according to the position of the robot and facilitates effectively performing of disinfection by the robot. In one disinfection square, the disinfecting planning point is one of the disinfecting consideration points. There are multiple disinfecting consideration points in each disinfection square, and there may be one disinfecting planning point, or there may be no disinfecting planning point.

Step S103: Determine a disinfection order of disinfecting targets corresponding to the disinfection squares according to distances between a position of the robot after the robot completes disinfection of one of the targets corresponding to one of the disinfection squares and to-be-disinfected ones of the disinfection squares.

After the disinfection grid is generated on the initial map, based on the position of the robot which can be the initial position of the robot, or the position of the robot after completing the disinfection of any disinfection square, the distances between the robot and the squares to be disinfected. The to-be-disinfected square that is closest to the robot can be selected as the next square where the robot performs disinfection to the target corresponding to the square. Alternatively, when the robot is at the initial position, the first disinfection square where the robot performs the disinfection to the target corresponding to the square can be determined according to the main direction.

For example, after completing the disinfection to a target corresponding to a disinfection square A, the robot is at the disinfecting planning point of the disinfection square A. The distances between the robot and other squares to be disinfected can then be calculated based on this position. A disinfection square B to be disinfected that is closest to the robot is then selected as the next square to be disinfected. Similarly, after the disinfection is performed to the target corresponding to the disinfection square B, based on the position of the disinfecting planning point of the disinfection square B, the next disinfection square closest to the robot can be found until disinfection is performed to the targets corresponding to all the to-be-disinfected squares.

When there are multiple squares to be disinfected are of the same distance with respect to the position of the robot, any one of the squares can be selected to calculate the disinfecting planning point.

The squares to be disinfected may refer to the remaining disinfection squares whose targets need to be disinfected during the disinfecting process of the robot. In the disinfection squares in the original map, the disinfection squares whose targets have been disinfected can be omitted. The disinfection squares in which the distances between the robot and its disinfecting planning points are infinite can be omitted. The disinfection squares in which the distances between their disinfecting consideration points and the disinfecting planning points that have been disinfected are less than a preset fourth threshold can be omitted.

The distance between the robot and one disinfection square may be the distance between the robot and the center point of the disinfection square.

Step S104: According to distances between the position and the disinfecting consideration points in to-be-disinfected ones of the disinfection squares, combined with priority levels of the disinfecting consideration points in to-be-disinfected ones of the disinfection squares, determine disinfecting planning points in the disinfection squares.

After the disinfection squares to be disinfected are determined, it needs to compare the disinfecting consideration points in the disinfection squares to be disinfected to determine the disinfection consideration points that can be used as the disinfection planning point. When no disinfecting consideration points are qualified as the disinfecting planning point, the disinfection squares corresponding to the disinfecting consideration points are removed from the squares to be disinfected, and the next disinfection square that needs to be disinfected is further searched. For example, the disinfection square that is the closest to the robot is used as the next disinfection square that needs to be disinfected.

In one embodiment, as shown in FIG. 3, the priority of the disinfecting consideration point located in the center may be higher than that of the disinfecting consideration points located in the midpoints of the perpendiculars from the center point of the disinfection square to the sides of the disinfection square. The priority of the disinfecting consideration points located in the midpoints of the perpendiculars from the center point of the disinfection square to the sides of the disinfection square may be higher than that of the disinfecting consideration points located in the midpoints of the line segments from the center point to the vertices of the disinfection square. That is, the priority of disinfecting consideration point 0 is higher than that of the disinfecting consideration points 1-4, and the priority of disinfecting consideration points 1-4 is higher than that of the disinfecting consideration points 5-8.

After the priority of each disinfecting consideration point is determined, the disinfecting planning point for the robot to perform disinfection can be selected based on the distances between the position of the robot and the disinfecting consideration points as well as the priorities of the disinfecting consideration points.

In the case when the distance from the position of the robot to each disinfecting consideration point is equal, the disinfecting consideration point with the highest priority will be selected (e.g., the center point of a disinfection square) as the disinfecting planning point.

The first distance from the position of the robot to the first-priority disinfecting consideration point 0 is denoted by d0. The second distances from the position of the robot to the second-priority disinfecting consideration points are denoted by d1, d2, d3 and d4, respectively. The minimum value of the second distances from the position of the robot to the second-priority disinfecting consideration points is denoted by d2 min=(d1, d2, d3, d4). If the difference between the first distance d0 and the minimum value d2 min of the second distances is less than a preset first threshold T1, the first-priority disinfecting consideration point 0 will be selected as the disinfecting planning point. If the difference between the first distance d0 and the minimum value d2 min of the second distances is greater than the preset first threshold T1, the second-priority disinfecting consideration point corresponding to the minimum value of the second distances will be selected as the disinfecting planning point. That is, if the robot is closer to the second-priority disinfecting consideration points than to the first-priority disinfecting consideration point 0, and the difference between the distance between the robot and the first-priority disinfecting consideration point and the smallest distance between the robot and the second-priority disinfecting consideration point is greater than a certain value, the second-priority disinfecting consideration point corresponding to the minimum value of the second distances is selected as the disinfecting planning point of the disinfection square.

In one embodiment, if the first-priority and the second-priority disinfecting consideration points of the in the disinfection square are in obstacle areas, the distance for the robot to reach the disinfecting consideration points of the first priority and the second priority is infinite. Then, the disinfecting planning point is selected from the third-priority disinfection consideration points The third distances between the third-priority disinfecting consideration points of and the robot is denoted by d5, d6, d7 and d8, respectively, and d3 min=min(d5, d6, d7 and d8) represents the minimum value of the third distances. When both the first distance and the second distances are infinite, the disinfecting consideration point corresponding to d3 min may be selected as the disinfecting planning point corresponding to the disinfection square.

If third distances between the third-priority disinfecting consideration points and the robot are infinite, which means that the third-priority disinfecting consideration points are in obstacle areas, the disinfection square will be omitted and calculation for the next to-be-disinfected square can be continued.

Step S105: Perform disinfection to the targets corresponding to the disinfection squares according to the disinfection order and the disinfecting planning points.

Through the disinfecting order of the disinfection squares determined according to the above-mentioned steps, combined with the disinfecting planning points in each disinfecting square in the determined disinfection order, the multiple target disinfecting planning points can be determined.

When the robot is moving to a target disinfecting planning point, since the robot may be constantly approaching obstacles, the position of the target disinfecting planning point that was originally accessible may be determined as being occupied by obstacles after approaching the target disinfecting planning point. Therefore, the original navigation planning path may change. In order to avoid the phenomenon that the robot finds that the target point is unreachable after approaching the target point, and then plans to move again, it can determine in real time whether the original target disinfecting planning point is reachable before each global path planning. If the current target disinfecting planning point is not reachable, the target disinfecting planning point may be updated to be the closest reachable point from the target disinfecting planning point. That is, the disinfecting planning point that is reachable and closest to the target disinfecting planning point is determined as the target disinfecting planning point. Thus, the movement of the robot is continuous and free from stuttering.

In one embodiment, when the robot arrives at a target disinfecting planning point, it can also first determine whether the target corresponding to the target disinfecting planning point needs to be disinfected. The fourth distances between the target disinfecting planning point and the completed historical disinfecting planning points can be compared with a preset second threshold. If one of the fourth distances is less than the second threshold, one of other disinfecting consideration points in the disinfecting square where the target disinfecting planning point is located is determined as the target disinfecting planning point. For example, the above-mentioned disinfecting consideration points in the disinfecting square where the target disinfecting planning point is located can be selected in the descending order of the distances between them and the robot. Calculation will be performed for each selected disinfecting planning point until the requirement of the preset second threshold is met.

When the list of to-be-disinfected squares is empty, or the number of to-be-disinfected squares reaches the threshold set by the user, the disinfecting task will be ended.

It should be understood that sequence numbers of the foregoing processes do not mean particular execution sequences. The execution sequences of the processes should be determined based on functions and internal logic of the processes, and should not be construed as any limitation on the implementation processes of this embodiment of the present disclosure.

Referring to FIG. 5, in one embodiment, a disinfection robot may include an initial map acquisition unit 401, a disinfecting square determination unit 402, a disinfecting order determination unit 403, a disinfecting planning point determination unit 404, and a disinfection unit 405. The initial map acquisition unit 401 is to obtain an initial map within a field of view of the robot at an initial position. The disinfecting square determination unit 402 is to generate a disinfection grid having a number of disinfection squares on the initial map, and determine a number of disinfecting consideration points in the disinfection squares. The disinfecting order determination unit 403 is to determine a disinfection order of disinfecting targets corresponding to the disinfection squares according to distances between a position of the robot after the robot completes disinfection of one of the targets corresponding to one of the disinfection squares and to-be-disinfected ones of the disinfection squares. The disinfecting planning point determination unit 404 is to, according to distances between the position and the disinfecting consideration points in to-be-disinfected ones of the disinfection squares, combined with priority levels of the disinfecting consideration points in to-be-disinfected ones of the disinfection squares, determine disinfecting planning points in the disinfection squares. The disinfection unit 405 is to perform disinfection to the targets corresponding to the disinfection squares according to the disinfection order and the disinfecting planning points.

It should be noted that the basic principles and technical effects of the path generation device are the same as the aforementioned method. For a brief description, for parts not mentioned in this device embodiment, reference can be made to corresponding description in the method embodiments.

It should be noted that content such as information exchange between the modules/units and the execution processes thereof is based on the same idea as the method embodiments of the present disclosure, and produces the same technical effects as the method embodiments of the present disclosure. For the specific content, refer to the foregoing description in the method embodiments of the present disclosure. Details are not described herein again.

Another aspect of the present disclosure is directed to a non-transitory computer-readable medium storing instructions which, when executed, cause one or more processors to perform the methods, as discussed above. The computer-readable medium may include volatile or non-volatile, magnetic, semiconductor, tape, optical, removable, non-removable, or other types of computer-readable medium or computer-readable storage devices. For example, the computer-readable medium may be the storage device or the memory module having the computer instructions stored thereon, as disclosed. In some embodiments, the computer-readable medium may be a disc or a flash drive having the computer instructions stored thereon.

It should be understood that the disclosed device and method can also be implemented in other manners. The device embodiments described above are merely illustrative. For example, the flowcharts and block diagrams in the accompanying drawings illustrate the architecture, functionality and operation of possible implementations of the device, method and computer program product according to embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition, functional modules in the embodiments of the present disclosure may be integrated into one independent part, or each of the modules may be independent, or two or more modules may be integrated into one independent part.

in addition, functional modules in the embodiments of the present disclosure may be integrated into one independent part, or each of the modules may exist alone, or two or more modules may be integrated into one independent part. When the functions are implemented in the form of a software functional unit and sold or used as an independent product, the functions may be stored in a computer-readable storage medium. Based on such an understanding, the technical solutions in the present disclosure essentially, or the part contributing to the prior art, or some of the technical solutions may be implemented in a form of a software product. The computer software product is stored in a storage medium and includes several instructions for instructing a computer device (which may be a personal computer, a server, a network device, or the like) to perform all or some of the steps of the methods described in the embodiments of the present disclosure. The foregoing storage medium includes: any medium that can store program code, such as a USB flash drive, a removable hard disk, a read-only memory (ROM), a random access memory (RAM), a magnetic disk, or an optical disc.

A person skilled in the art can clearly understand that for the purpose of convenient and brief description, for specific working processes of the device, modules and units described above, reference may be made to corresponding processes in the embodiments of the foregoing method, which are not repeated herein.

In the embodiments above, the description of each embodiment has its own emphasis. For parts that are not detailed or described in one embodiment, reference may be made to related descriptions of other embodiments.

A person having ordinary skill in the art may clearly understand that, for the convenience and simplicity of description, the division of the above-mentioned functional units and modules is merely an example for illustration. In actual applications, the above-mentioned functions may be allocated to be performed by different functional units according to requirements, that is, the internal structure of the device may be divided into different functional units or modules to complete all or part of the above-mentioned functions. The functional units and modules in the embodiments may be integrated in one processing unit, or each unit may exist alone physically, or two or more units may be integrated in one unit. The above-mentioned integrated unit may be implemented in the form of hardware or in the form of software functional unit. In addition, the specific name of each functional unit and module is merely for the convenience of distinguishing each other and are not intended to limit the scope of protection of the present disclosure. For the specific operation process of the units and modules in the above-mentioned system, reference may be made to the corresponding processes in the above-mentioned method embodiments, and are not described herein.

A person having ordinary skill in the art may clearly understand that, the exemplificative units and steps described in the embodiments disclosed herein may be implemented through electronic hardware or a combination of computer software and electronic hardware. Whether these functions are implemented through hardware or software depends on the specific application and design constraints of the technical schemes. Those ordinary skilled in the art may implement the described functions in different manners for each particular application, while such implementation should not be considered as beyond the scope of the present disclosure.

In the embodiments provided by the present disclosure, it should be understood that the disclosed apparatus (device)/terminal device and method may be implemented in other manners. For example, the above-mentioned apparatus (device)/terminal device embodiment is merely exemplary. For example, the division of modules or units is merely a logical functional division, and other division manner may be used in actual implementations, that is, multiple units or components may be combined or be integrated into another system, or some of the features may be ignored or not performed. In addition, the shown or discussed mutual coupling may be direct coupling or communication connection, and may also be indirect coupling or communication connection through some interfaces, devices or units, and may also be electrical, mechanical or other forms.

The units described as separate parts may or may not be physically separate, and parts displayed as units may or may not be physical units, may be located in one position, or may be distributed on a plurality of network units. Some or all of the modules may be selected according to actual requirements to achieve the objectives of the solutions of the embodiments.

The functional units and modules in the embodiments may be integrated in one processing unit, or each unit may exist alone physically, or two or more units may be integrated in one unit. The above-mentioned integrated unit may be implemented in the form of hardware or in the form of software functional unit.

When the integrated module/unit is implemented in the form of a software functional unit and is sold or used as an independent product, the integrated module/unit may be stored in a non-transitory computer-readable storage medium. Based on this understanding, all or part of the processes in the method for implementing the above-mentioned embodiments of the present disclosure may also be implemented by instructing relevant hardware through a computer program. The computer program may be stored in a non-transitory computer-readable storage medium, which may implement the steps of each of the above-mentioned method embodiments when executed by a processor. In which, the computer program includes computer program codes which may be the form of source codes, object codes, executable files, certain intermediate, and the like. The computer-readable medium may include any primitive or device capable of carrying the computer program codes, a recording medium, a USB flash drive, a portable hard disk, a magnetic disk, an optical disk, a computer memory, a read-only memory (ROM), a random-access memory (RAM), electric carrier signals, telecommunication signals and software distribution media. It should be noted that the content contained in the computer readable medium may be appropriately increased or decreased according to the requirements of legislation and patent practice in the jurisdiction. For example, in some jurisdictions, according to the legislation and patent practice, a computer readable medium does not include electric carrier signals and telecommunication signals.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A computer-implemented navigation method for a disinfection robot, the method comprising:
obtaining an initial map within a field of view of the robot at an initial position;
generating a disinfection grid having a plurality of disinfection squares on the initial map, and determining a plurality of disinfecting consideration points in the disinfection squares;
determining a disinfection order of disinfecting targets corresponding to the disinfection squares according to distances between a position of the robot after the robot completes disinfection of one of the targets corresponding to one of the disinfection squares and to-be-disinfected ones of the disinfection squares;
according to distances between the position and the disinfecting consideration points in to-be-disinfected ones of the disinfection squares, combined with priority levels of the disinfecting consideration points in to-be-disinfected ones of the disinfection squares, determining disinfecting planning points in the disinfection squares, wherein each of the disinfection squares comprises the disinfecting consideration points, different priority levels are set to the disinfecting consideration points according to positions of the disinfecting consideration points in corresponding disinfection squares, and wherein the disinfecting consideration points within a same disinfection square have different priority levels; and
performing disinfection to the targets corresponding to the disinfection squares according to the disinfection order and the disinfecting planning points.

2. The method of claim 1, further comprising, before determining the disinfection order of disinfecting targets corresponding to the disinfection squares,
determining distances between the position of the robot and the disinfecting consideration points in the disinfection squares; and
determining which of the disinfection squares are to-be-disinfected disinfection squares according to the distances between the position of the robot and the disinfecting consideration points in the disinfection squares.

3. The method of claim 1, wherein the disinfecting consideration points comprise first-priority disinfecting consideration points, second-priority disinfecting consideration points, and third-priority disinfecting consideration points.

4. The method of claim 3, wherein the first-priority disinfecting consideration points are located in centers of the disinfection squares, the second-priority disinfecting consideration points are located in center points of perpendiculars from the centers of the disinfection squares to sides of the disinfection squares, and the third-priority disinfecting consideration points are located in center points of line segments from the centers of the disinfection squares to the vertices of the disinfection squares; and
wherein the first-priority disinfecting consideration points have a higher priority than the second-priority disinfecting consideration points, and the second-priority disinfecting consideration points have a higher priority than the third-priority disinfecting consideration points.

5. The method of claim 3, wherein determining disinfecting planning points in the disinfection squares comprises:
determining first distances between the position of the robot and the first-priority disinfecting consideration points, and second distances between the position of the robot and the second-priority disinfecting consideration points;
in response to differences between the first distances and minimum values of the second distances being less than a first threshold, determining the first-priority disinfecting consideration points as the disinfecting planning points of the disinfection squares;
in response to differences between the first distances and the minimum values of the second distances being greater than or equal to the first threshold, determining the disinfecting consideration points corresponding to minimum values of the second distances as the disinfecting planning points of the disinfection squares; and
in response to the first distance and the second distance being infinite, determining third distances between the position of the robot and the third-priority disinfecting consideration points, and selecting the disinfecting consideration point corresponding to minimum values of the third distances as the disinfecting planning point of the disinfection grid, wherein the initial map comprises: obstacle areas and free-moving areas, and wherein the first distance is infinite when the first-priority disinfecting consideration point is in the obstacle areas, and the second distance is infinite when the second-priority disinfecting consideration point is in the obstacle areas.

6. The method of claim 1, wherein, in each of the disinfection squares, the disinfecting planning point is one of the disinfecting consideration points, and wherein not all disinfection squares have the disinfecting planning point; and
wherein performing disinfection to the targets corresponding to the disinfection squares according to the disinfection order and the disinfecting planning points comprises:
determining whether a current target disinfecting planning point is reachable;
in response to the current target disinfecting planning point being not reachable, updating the current target disinfecting planning point to be a reachable point closest to the current target disinfecting planning point.

7. The method of claim 6, performing disinfection to the targets corresponding to the disinfection squares according to the disinfection order and the disinfecting planning points comprises:
a) in response to the robot reaching the current target disinfecting planning point, determining fourth distances between the current target disinfecting planning point and historical disinfecting planning points where disinfection has been performed; and
b) in response to the fourth distances being less than a second threshold, updating one of remaining disinfecting consideration points in the disinfection square where the current target disinfecting planning point is located to be current target disinfecting planning point, and returning to a).

8. A disinfection robot comprising:
one or more processors; and
a memory coupled to the one or more processors, the memory storing programs that, when executed by the one or more processors, cause performance of operations comprising:
obtaining an initial map within a field of view of the robot at an initial position;
generating a disinfection grid having a plurality of disinfection squares on the initial map, and determining a plurality of disinfecting consideration points in the disinfection squares;

determining a disinfection order of disinfecting targets corresponding to the disinfection squares according to distances between a position of the robot after the robot completes disinfection of one of the targets corresponding to one of the disinfection squares and to-be-disinfected ones of the disinfection squares;

according to distances between the position and the disinfecting consideration points in to-be-disinfected ones of the disinfection squares, combined with priority levels of the disinfecting consideration points in to-be-disinfected ones of the disinfection squares, determining disinfecting planning points in the disinfection squares, wherein each of the disinfection squares comprises the disinfecting consideration points, different priority levels are set to the disinfecting consideration points according to positions of the disinfecting consideration points in corresponding disinfection squares, and wherein the disinfecting consideration points within a same disinfection square have different priority levels; and performing disinfection to the targets corresponding to the disinfection squares according to the disinfection order and the disinfecting planning points.

9. The robot of claim 8, wherein the operations further comprise, before determining the disinfection order of disinfecting targets corresponding to the disinfection squares, determining distances between the position of the robot and the disinfecting consideration points in the disinfection squares; and determining which of the disinfection squares are to-be-disinfected disinfection squares according to the distances between the position of the robot and the disinfecting consideration points in the disinfection squares.

10. The robot of claim 8, wherein the disinfecting consideration points comprise first-priority disinfecting consideration points, second-priority disinfecting consideration points, and third-priority disinfecting consideration points.

11. The robot of claim 10, wherein the first-priority disinfecting consideration points are located in centers of the disinfection squares, the second-priority disinfecting consideration points are located in center points of perpendiculars from the centers of the disinfection squares to sides of the disinfection squares, and the third-priority disinfecting consideration points are located in center points of line segments from the centers of the disinfection squares to the vertices of the disinfection squares.

12. The robot of claim 10, wherein determining disinfecting planning points in the disinfection squares comprises:

determining first distances between the position of the robot and the first-priority disinfecting consideration points, and second distances between the position of the robot and the second-priority disinfecting consideration points;

in response to differences between the first distances and minimum values of the second distances being less than a first threshold, determining the first-priority disinfecting consideration points as the disinfecting planning points of the disinfection squares;

in response to differences between the first distances and the minimum values of the second distances being greater than or equal to the first threshold, determining the disinfecting consideration points corresponding to minimum values of the second distances as the disinfecting planning points of the disinfection squares; and in response to the first distance and the second distance being infinite, determining third distances between the position of the robot and the third-priority disinfecting consideration points, and selecting the disinfecting consideration point corresponding to minimum values of the third distances as the disinfecting planning point of the disinfection grid, wherein the initial map comprises: obstacle areas and free-moving areas, and wherein the first distance is infinite when the first-priority disinfecting consideration point is in the obstacle areas, and the second distance is infinite when the second-priority disinfecting consideration point is in the obstacle areas.

13. The robot of claim 8, wherein performing disinfection to the targets corresponding to the disinfection squares according to the disinfection order and the disinfecting planning points comprises:

determining whether a current target disinfecting planning point is reachable;

in response to the current target disinfecting planning point being not reachable, updating the current target disinfecting planning point to be a reachable point closest to the current target disinfecting planning point.

14. The method of claim 13, performing disinfection to the targets corresponding to the disinfection squares according to the disinfection order and the disinfecting planning points comprises:

a) in response to the robot reaching the current target disinfecting planning point, determining fourth distances between the current target disinfecting planning point and historical disinfecting planning points where disinfection has been performed; and b) in response to the fourth distances being less than a second threshold, updating one of remaining disinfecting consideration points in the disinfection square where the current target disinfecting planning point is located to be current target disinfecting planning point, and returning to a).

15. A non-transitory computer-readable storage medium storing instructions that, when executed by at least one processor of a disinfection robot, cause the at least one processor to perform a method, the method comprising:

obtaining an initial map within a field of view of the robot at an initial position;

generating a disinfection grid having a plurality of disinfection squares on the initial map, and determining a plurality of disinfecting consideration points in the disinfection squares;

determining a disinfection order of disinfecting targets corresponding to the disinfection squares according to distances between a position of the robot after the robot completes disinfection of one of the targets corresponding to one of the disinfection squares and to-be-disinfected ones of the disinfection squares;

according to distances between the position and the disinfecting consideration points in to-be-disinfected ones of the disinfection squares, combined with priority levels of the disinfecting consideration points in to-be-disinfected ones of the disinfection squares, determining disinfecting planning points in the disinfection squares, wherein each of the disinfection squares comprises the disinfecting consideration points, different priority levels are set to the disinfecting consideration points according to positions of the disinfecting consideration points in corresponding disinfection squares, and wherein the disinfecting consideration points within a same disinfection square have different priority levels; and performing disinfection to the targets corresponding to the disinfection squares according to the disinfection order and the disinfecting planning points.

16. The non-transitory computer-readable storage medium of claim 15, further comprising, before determining the disinfection order of disinfecting targets corresponding to the disinfection squares,
determining distances between the position of the robot and the disinfecting consideration points in the disinfection squares; and
determining which of the disinfection squares are to-be-disinfected disinfection squares according to the distances between the position of the robot and the disinfecting consideration points in the disinfection squares.

17. The non-transitory computer-readable storage medium of claim 15, wherein the disinfecting consideration points comprise first-priority disinfecting consideration points, second-priority disinfecting consideration points, and third-priority disinfecting consideration points.

18. The non-transitory computer-readable storage medium of claim 17, wherein the first-priority disinfecting consideration points are located in centers of the disinfection squares, the second-priority disinfecting consideration points are located in center points of perpendiculars from the centers of the disinfection squares to sides of the disinfection squares, and the third-priority disinfecting consideration points are located in center points of line segments from the centers of the disinfection squares to the vertices of the disinfection squares.

19. The non-transitory computer-readable storage medium of claim 17, wherein determining disinfecting planning points in the disinfection squares comprises:
determining first distances between the position of the robot and the first-priority disinfecting consideration points, and second distances between the position of the robot and the second-priority disinfecting consideration points;
in response to differences between the first distances and minimum values of the second distances being less than a first threshold, determining the first-priority disinfecting consideration points as the disinfecting planning points of the disinfection squares;
in response to differences between the first distances and the minimum values of the second distances being greater than or equal to the first threshold, determining the disinfecting consideration points corresponding to minimum values of the second distances as the disinfecting planning points of the disinfection squares; and
in response to the first distance and the second distance being infinite, determining third distances between the position of the robot and the third-priority disinfecting consideration points, and selecting the disinfecting consideration point corresponding to minimum values of the third distances as the disinfecting planning point of the disinfection grid, wherein the initial map comprises: obstacle areas and free-moving areas, and wherein the first distance is infinite when the first-priority disinfecting consideration point is in the obstacle areas, and the second distance is infinite when the second-priority disinfecting consideration point is in the obstacle areas.

20. The non-transitory computer-readable storage medium of claim 15, wherein performing disinfection to the targets corresponding to the disinfection squares according to the disinfection order and the disinfecting planning points comprises:
determining whether a current target disinfecting planning point is reachable;
in response to the current target disinfecting planning point being not reachable, updating the current target disinfecting planning point to be a reachable point closest to the current target disinfecting planning point.

* * * * *